(12) United States Patent
Matsumoto

(10) Patent No.: US 9,412,047 B2
(45) Date of Patent: Aug. 9, 2016

(54) MEDICAL INFORMATION PROCESSING APPARATUS

(71) Applicant: Konica Minolta, Inc., Tokyo (JP)

(72) Inventor: Hiroaki Matsumoto, Yokohama (JP)

(73) Assignee: KONICA MINOLTA, INC., Tokyo (JP)

( * ) Notice: Subject to any disclaimer, the term of this patent is extended or adjusted under 35 U.S.C. 154(b) by 0 days.

(21) Appl. No.: 14/539,309

(22) Filed: Nov. 12, 2014

(65) Prior Publication Data

US 2015/0146947 A1 May 28, 2015

(30) Foreign Application Priority Data

Nov. 22, 2013 (JP) ................................. 2013-241829

(51) Int. Cl.
| | | |
|---|---|---|
| *G06K 9/00* | (2006.01) | |
| *G06K 9/62* | (2006.01) | |
| *G06F 19/00* | (2011.01) | |
| *G06T 7/00* | (2006.01) | |

(52) U.S. Cl.
CPC ............ *G06K 9/6267* (2013.01); *G06F 19/321* (2013.01); *G06K 9/6253* (2013.01); *G06K 2209/051* (2013.01); *G06T 7/0012* (2013.01)

(58) Field of Classification Search
None
See application file for complete search history.

(56) References Cited

U.S. PATENT DOCUMENTS

| | | | | |
|---|---|---|---|---|
| 6,674,879 | B1 * | 1/2004 | Weisman | A61B 8/06 378/94 |
| 2006/0274928 | A1 * | 12/2006 | Collins | A61B 6/00 382/132 |
| 2007/0237377 | A1 * | 10/2007 | Oosawa | G06F 19/321 382/128 |
| 2009/0228299 | A1 * | 9/2009 | Kangarloo | G06F 19/321 705/2 |
| 2012/0014559 | A1 * | 1/2012 | Suehling | G06K 9/6207 382/103 |
| 2014/0022250 | A1 * | 1/2014 | Mansi | A61B 19/50 345/420 |
| 2015/0193966 | A1 * | 7/2015 | Sakuragi | G06T 19/20 348/46 |

* cited by examiner

*Primary Examiner* — Shervin Nakhjavan
(74) *Attorney, Agent, or Firm* — Lucas & Mercanti, LLP

(57) ABSTRACT

Disclosed is a medical information processing apparatus including a medical information storage unit in which a piece of position information in a model image of a human body and a piece of medical information are stored, a first display control unit which displays a medical image, a specifying unit which specifies a focus position in the medical image, an extraction unit which converts a piece of position information of the focus position into a piece of position information in the model image and which extracts a piece of medical information corresponding to the piece of position information in the model image from the medical information storage unit, a second display control unit which displays the piece of medical information as a selection candidate, a selection unit which selects a piece of medical information, and a creation unit which creates an interpretation report by using the piece of medical information.

8 Claims, 11 Drawing Sheets

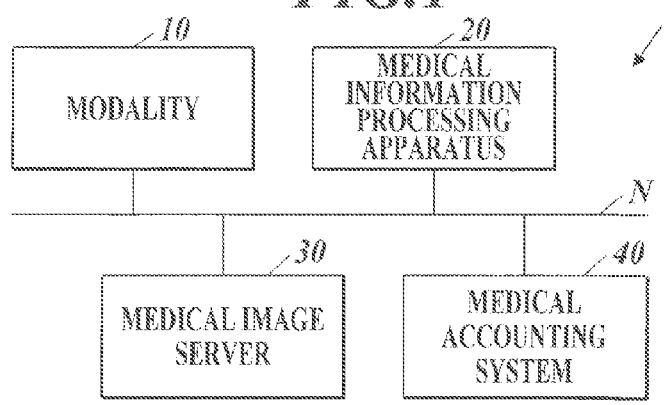
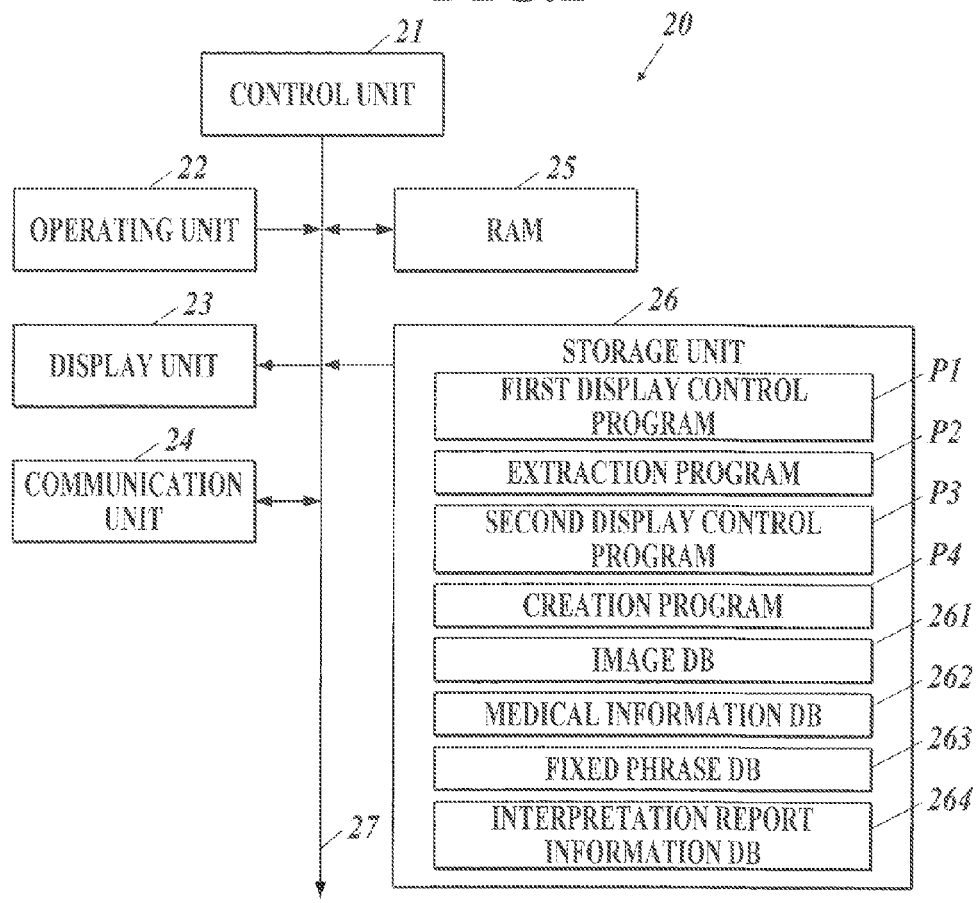

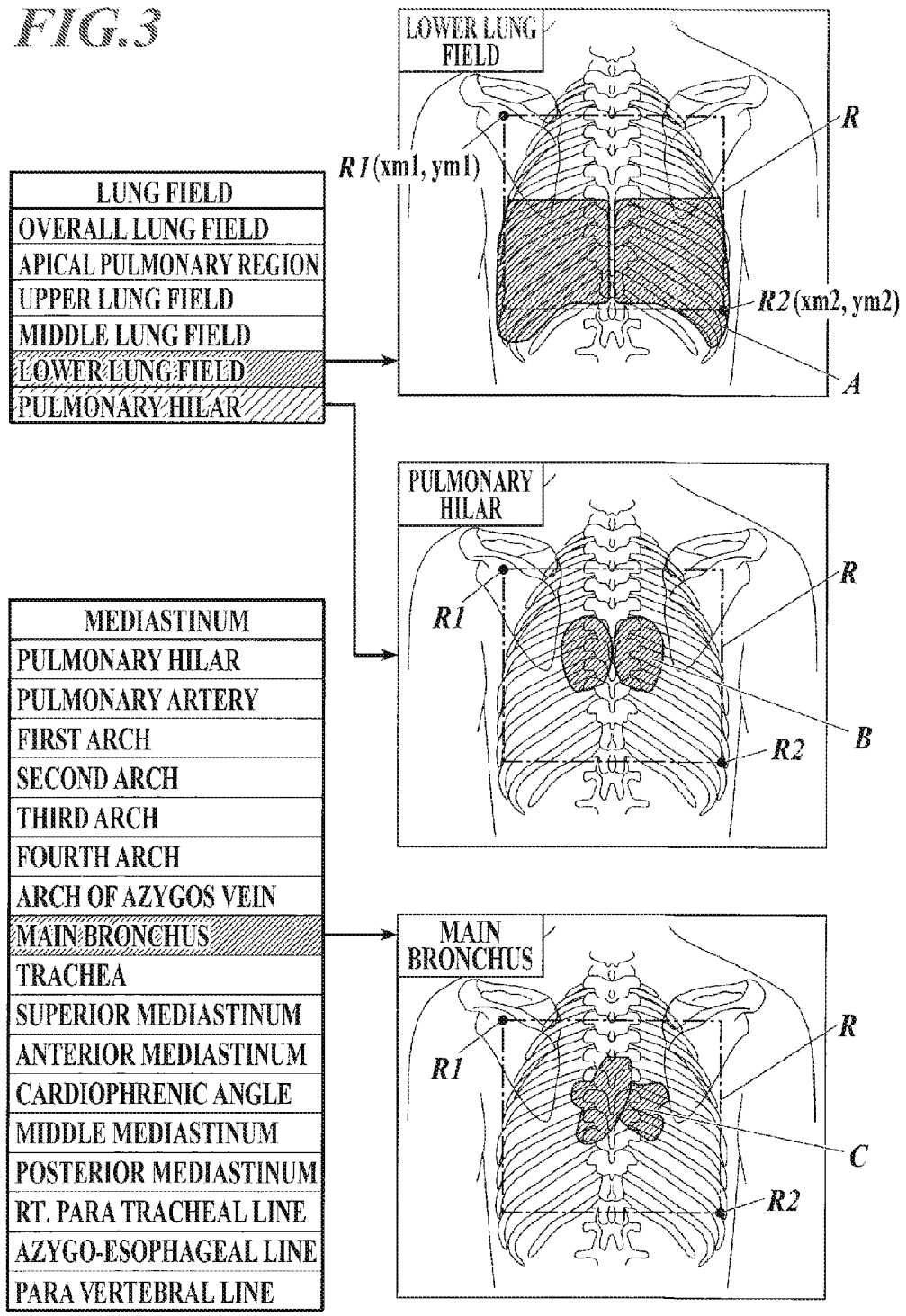

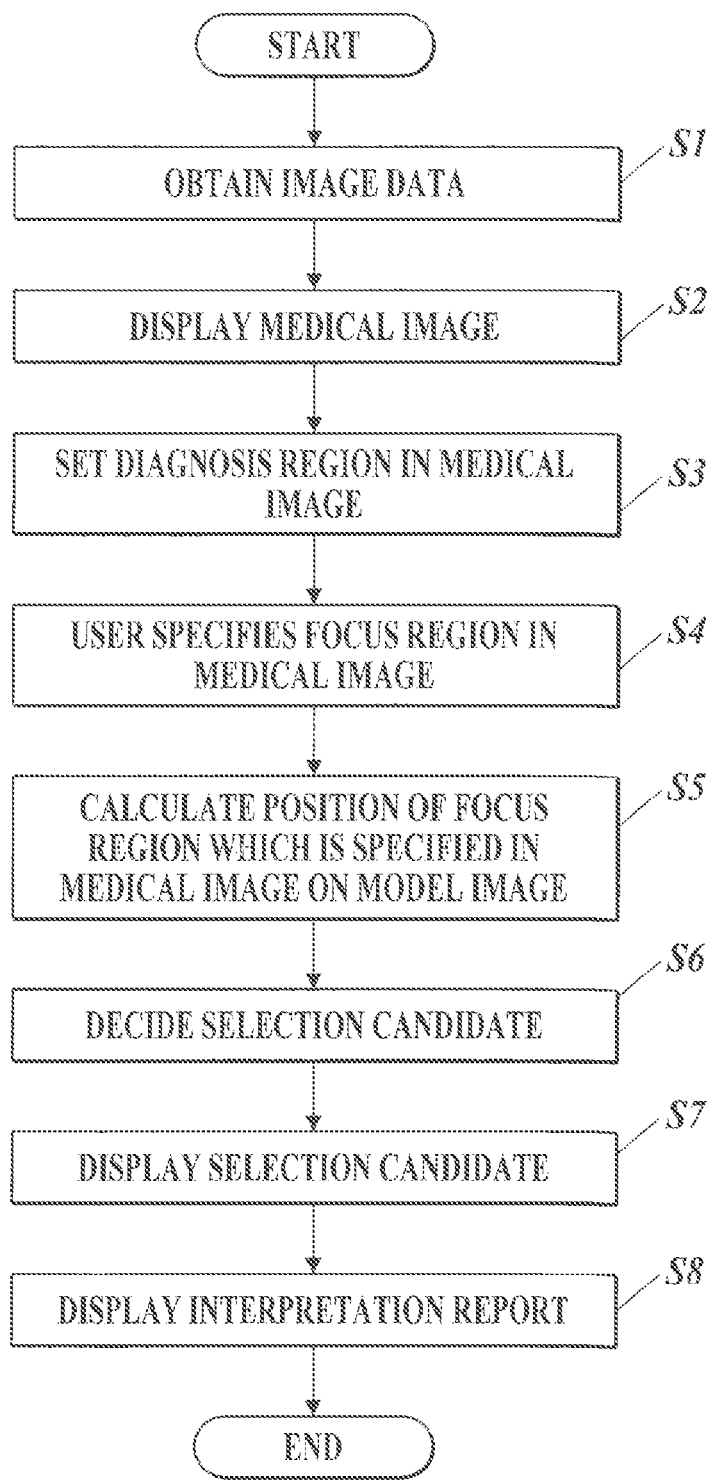

FIG. 5

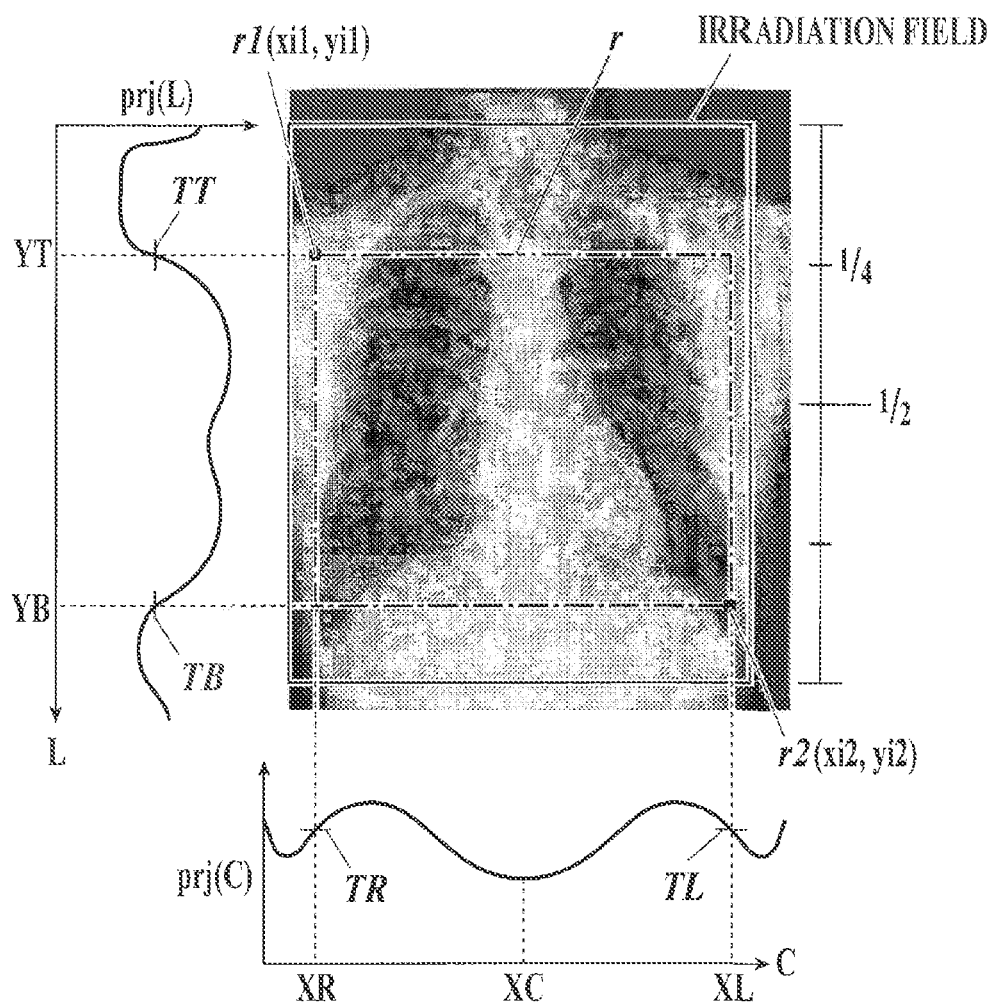

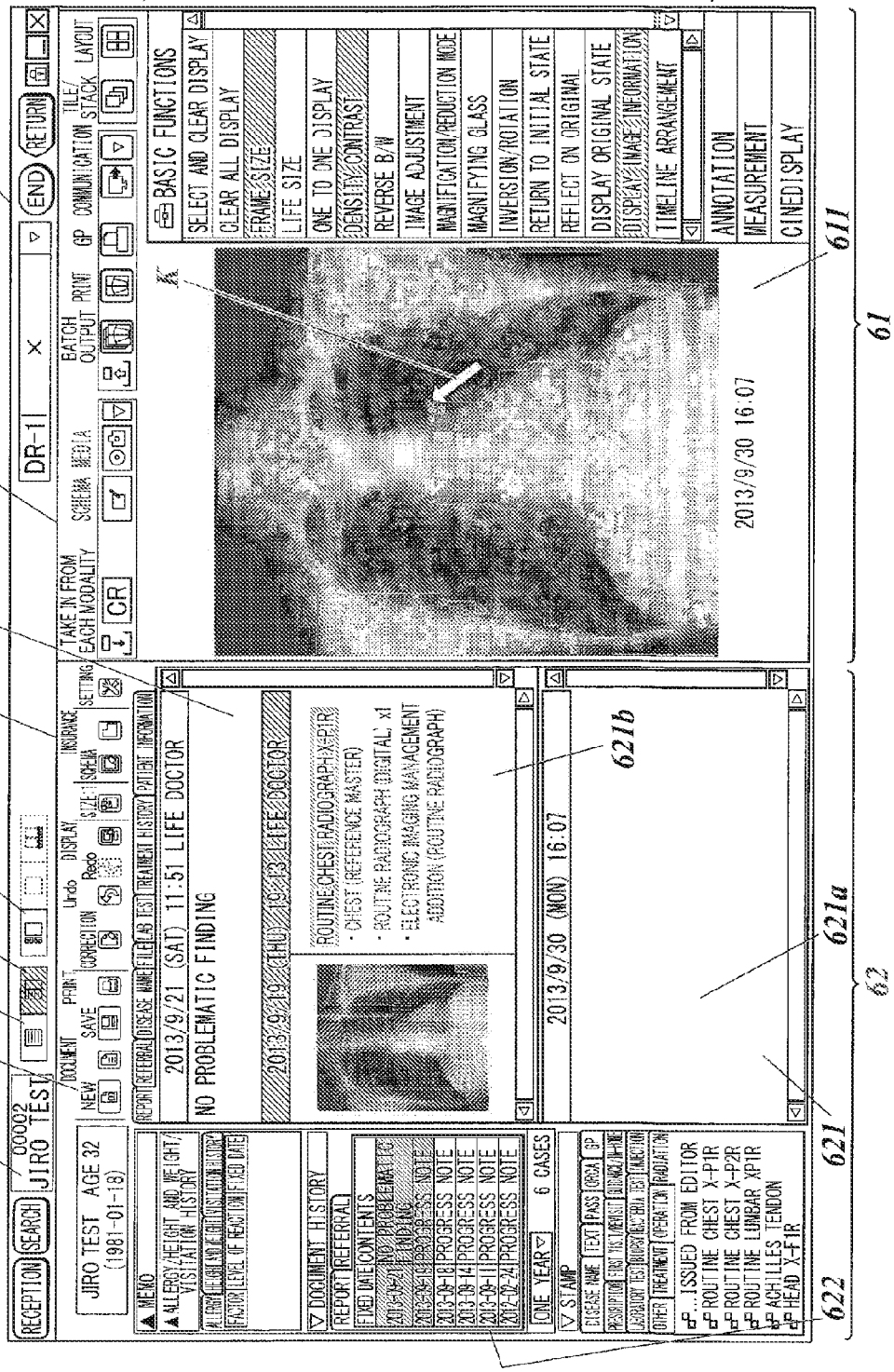

FIG. 10

MEDICAL INFORMATION PROCESSING APPARATUS

BACKGROUND OF THE INVENTION

1. Field of the Invention

The present invention relates to a medical information processing apparatus.

2. Description of Related Art

In the medical field, image reading is performed by displaying medical images generated in various modalities and by a physician observing the condition of a lesion. Then, the physician who performed the image reading creates an interpretation report which includes his/her findings relating to the image on the interpretation report creation screen.

Such interpretation report includes plurality of items which should be input, such as type of lesion, anatomical section, level, condition, conclusion and the like and this causes great burden on the physician who creates an interpretation report.

To help creation of interpretation reports, for example, there is suggested a technique to create an interpretation report by detecting an abnormality in image data and using the combination of the type of the detected abnormality and its position (see JP 3332104, for example). Further, there is suggested a technique to create an interpretation report by searching a case which is similar to the diagnosis target image of the patient from his/her past cases and using the report of the similar case (see JP 5128154, for example).

However, in the techniques described in JP 3332104 and JP 5128154, since anatomical sections and abnormal shadows in image data are recognized by image analysis, there is a possibility that image analysis may fail depending on the image condition due to the disease condition of the subject. In such case, an appropriate interpretation report cannot be created and as a result, workload of interpretation report creation cannot be reduced.

Further, in the techniques described in JP 3332104 and JP 5128154, the processing of image analysis and the like takes time due to narrowing down of the anatomical sections and abnormal shadows if there are great number of anatomical sections and lesions to cover various types of anatomical sections and lesions. Therefore, there has been a problem such that a physician cannot start image reading and interpretation report creation right after a medical image is captured.

SUMMARY OF THE INVENTION

In view of the above problems, an object of the present invention is to provide a medical information processing apparatus in which image reading and interpretation report creation can be started right after image capturing and which can reduce the workload of interpretation report creation.

To achieve at least one of the abovementioned objects, according to an aspect, a medical information processing apparatus reflecting one aspect of the present invention includes a medical information storage unit in which a piece of position information in a model image of a human body, the piece of position information being set in advance, and a piece of medical information are stored so as to be associated with each other, a first display control unit which displays a medical image in a display unit, a specifying unit which specifies a focus position in the medical image displayed in the display unit, an extraction unit which converts a piece of position information of the focus position specified by the specifying unit into a piece of position information in the model image and which extracts a piece of medical information corresponding to the piece of position information in the model image from the medical information storage unit, a second display control unit which displays the piece of medical information extracted by the extraction unit in the display unit as a selection candidate, a selection unit which selects a piece of medical information from the selection candidates displayed in the display unit, and a creation unit which creates an interpretation report by using the piece of medical information selected by the selection unit.

Preferably, the medical information processing apparatus further includes a set phrase storage unit in which a set phrase is stored, the set phrase being set in advance, and when the selection unit selects the piece of medical information from the selection candidates displayed in the display unit, the creation unit creates a text by combining the selected piece of medical information and the set phrase stored in the set phrase storage unit.

Preferably, a reference region which defines an anatomical region which is used as a reference is set in the model image in advance, and the extraction unit makes an anatomical region recognized in the medical image and the reference region set in the model image be associated to each other and converts the piece of position information of the focus position in the medical image into a piece of position information in the model image.

Preferably, the medical image is a chest image of a human body, and the anatomical region recognized in the medical image is a region including a thorax.

Preferably, the extraction unit decides order of priority of the pieces of medical information extracted as the selection candidates on a basis of predetermined priority level values, and the second display control unit displays the selection candidates in the display unit according to the order of priority.

Preferably, the predetermined priority level values are priority level values set in advance by a user, priority level values based on frequency of usage in past or priority level values obtained according to the specified focus position.

Preferably, the first display control unit displays an image display screen for displaying the medical image and a report creation screen for displaying the interpretation report simultaneously in the display unit.

BRIEF DESCRIPTION OF THE DRAWINGS

The above and other objects, advantages and features of the present invention will become more fully understood from the detailed description given hereinbelow and the appended drawings which are given byway of illustration only, and thus are not intended as a definition of the limits of the present invention, and wherein:

FIG. 1 is a view of system configuration of a diagnosis system;

FIG. 2 is a block diagram showing a functional configuration of a medical information processing apparatus;

FIG. 3 is a view for explaining medical information stored in a medical information DB;

FIG. 4 is a diagram showing an operation flow in the medical information processing apparatus;

FIG. 5 is a view showing an example of a report viewer screen;

FIG. 6 is a view for explaining a method for setting a diagnosis region in a medical image;

FIG. 7 is a view showing an example of a state where a focus position is specified in an medical image;

FIG. 10 is a view showing an example of a state where a selection dialog is shown in a repot viewer screen;

DESCRIPTION OF THE PREFERRED EMBODIMENTS

Figure 8A:
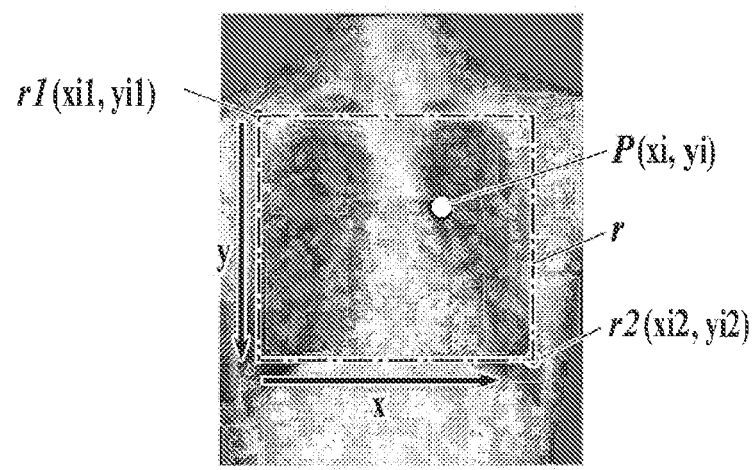
FIG. 8A is a view for explaining a process to calculate the position of the focus position in the medical image in a model image.

Hereinafter, a preferred embodiment of the present invention will be described with reference to the drawings. However, the scope of the invention is not limited to the illustrated examples.

[Configuration of Diagnosis System]

FIG. 1 shows an example of an overall configuration of a diagnosis system 1 according to the embodiment.

The diagnosis system 1 is a system applied to relatively small scale medical facilities such as a private practitioner's office, a clinic or such like. As shown in FIG. 1, the diagnosis system 1 includes a modality 10, a medical information processing apparatus 20, a medical image server 30 and a medical accounting system 40. Individual apparatuses that constitute the diagnosis system 1 are connected via a communication network N such as LAN (Local Area Network) so as to perform data communication with one another.

The modality 10 is provided in an image capturing room and is an image generating apparatus which picks up an image of a diagnosis target part of a patient and generates a digital medical image. As the modality 10, X-ray image capturing apparatuses such as a CR (Computed Radiography) apparatus, an FPD (Flat Panel Detector) apparatus and the like and an ultrasound diagnosis apparatus (US) can be applied.

In the embodiment, the modality 10 generates a medical image in DICOM (Digital Imaging and COmmmnication in Medicine) format. A medical image of DICOM format consists of an image portion and a header portion. In the image portion, image data of a medical image is written. In the header portion, supplementary information relating to the medical image is written in a description format defined by DICOM SR (Structured Reporting) standard. Supplementary information includes information such as patient information (patient ID, patient name, gender, age, date of birth, etc.) image pickup conditions (modality type, image pickup part, image pickup direction, image ID, various parameters, etc.) and date.

The medical information processing apparatus 20 is provided in an exam room and is a computer apparatus having an image viewer function and an interpretation report creation function.

Figure 5:
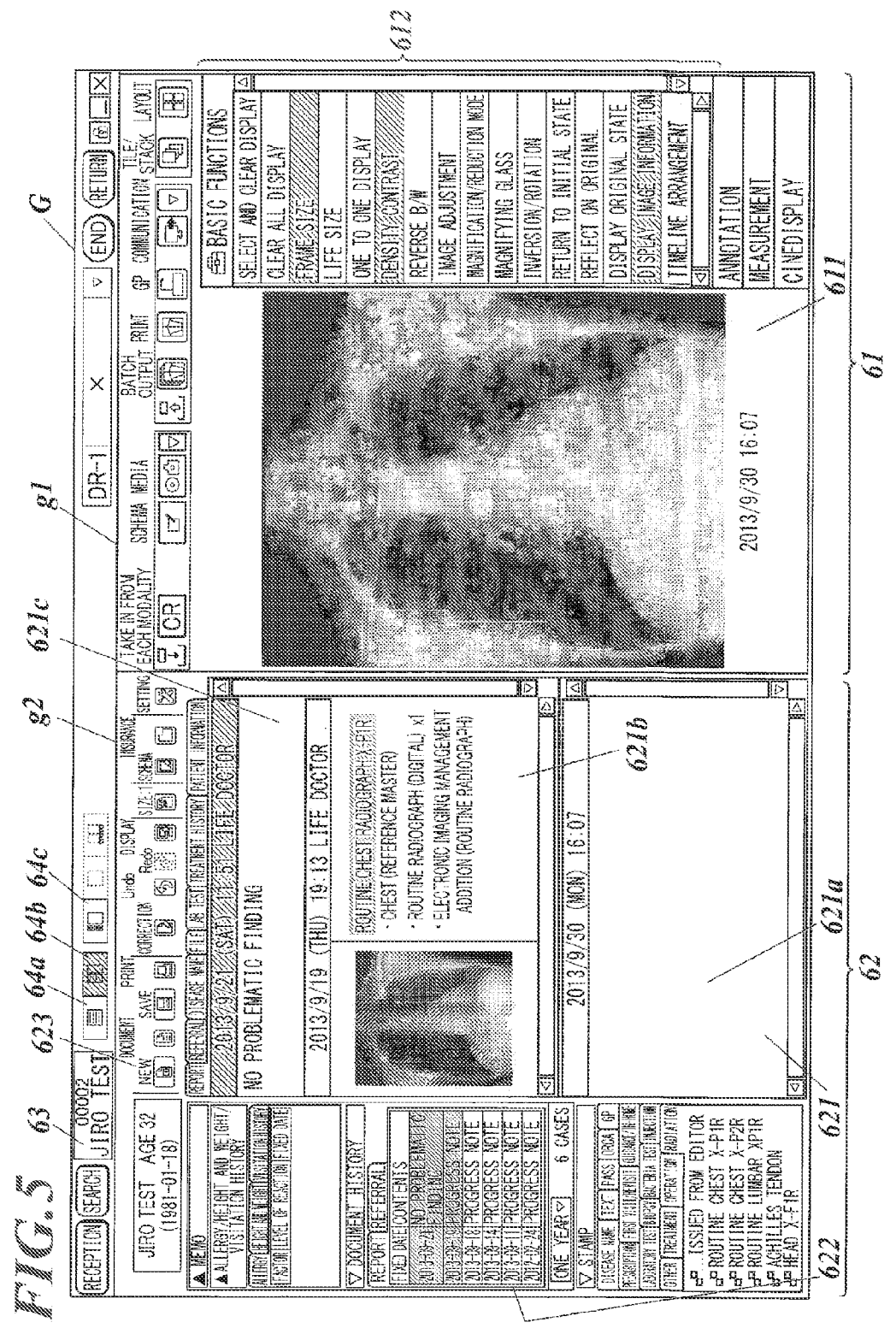

The medical information processing apparatus 20 is able to recognize supplementary information included in a medical image (a DICOM format medical image) which is generated in the modality 10. The medical information processing apparatus 20 stores and manages medical images and also displays a medical image on a viewer screen g1 (see FIG. 5) to perform various processing on the medical image according to operations through the viewer screen g1.

Further, the medical information processing apparatus 20 performs various processing relating to an interpretation report such as displaying an interpretation report creation screen g2 (see FIG. 5) which is for creating an interpretation report on findings and observations with respect to the medical image displayed on the viewer screen g1, storing information relating to the interpretation report (interpretation report information) created on the interpretation report creation screen g2, and sending the information included in the interpretation report information to the medical accounting system 40.

The medical image server 30 includes a medical image DB (Database) which is not shown in the drawings. The medical image server 30 stores and manages image data of the medical images generated in the modality 10. As the medical image server 30, PACS (Picture Archiving and Communication System) and the like can be applied. The medical image server 30, according to an obtaining request of image data from an outer device, sends the requested image data to the outer device.

The medical accounting system 40 is a computer apparatus for performing payment calculation, NHI point calculation and such like. The medical accounting system 40 receives information sent from the medical information processing apparatus 20. The medical accounting system 40 calculates health care fee points based on medical procedure information included in the received information, performs payment calculation and NHI point calculation and generates receipt data.

Here, the number of apparatuses constituting the diagnosis system 1 is not limited.

Further, as for the communication method in the diagnosis system 1, DICOM standard is generally used, and DICOM MWM (Modality Worklist Management) or DICOM MPPS (Modality Performed Procedure Step) is used for communication between apparatuses.

[Configuration of Medical Information Processing Apparatus]

FIG. 2 shows a functional configuration of the medical information processing apparatus 20.

As shown in FIG. 2, the medical information processing apparatus 20 includes a control unit 21, an operating unit (specifying unit) 22, a display unit 23, a communication unit 24, a RAM (Random Access Memory) 25, a storage unit 26, etc. and the units are connected by a bus 27.

The control unit 21 includes a CPU (Central Processing Unit) and the like and integrally controls processing operations of the units in the medical information processing apparatus 20. In particular, according to operation signals input from the operating unit 22 and instruction signals received by the communication unit 24, the CPU reads out various processing programs which are stored in the storage unit 26 and opens the programs in the RAM 25. In such way, the control unit 21 performs various processing in cooperation with the programs.

The operating unit 22 includes a keyboard including a cursor key, number input keys and various function keys, a pointing device such as a mouse and the like, and the operating unit 21 outputs operation signals which are input by key operation on the key board and the mouse operation to the control unit 21.

Further, the operating unit 22 may include a touch panel having electrodes arranged in lattice so as to cover the surface of the display unit 23 and may detect the position pushed by a finger or a touch pen and output the position information as operation information to the control unit 21.

The display unit 23 includes a monitor such as a LCD (Liquid Crystal Display), and according to instructions based on displaying signals input from the control unit 21, the display unit 23 displays various screen such as report viewer screens G and the like of individual patients, for example. Although it will be described later, a report viewer screen G is a screen in which a viewer screen (image display screen) g1 and an interpretation report creation screen (report creation screen) g2 are displayed simultaneously.

The communication unit 24 includes a network interface and performs sending and receiving data with an outer device which is connected via a communication network N. For example, the communication unit 24 receives image data of a medical image from the medical image server 30. Further, the communication unit 24 receives image data of a medical image which is obtained by picking up an image of a patient from the modality 10. Furthermore, the communication unit 24 sends various information and the like included in interpretation report information to the medical accounting system 40.

The RAM 25 forms a work area for temporarily storing various programs which are read out from the storage unit 26, input or output data, parameters, etc. during various processing which are controlled to be executed by the control unit 21.

The storage unit 26 includes a HDD (Hard Disk Drive), a non-volatile memory and the like, and stores various processing programs and data required for executing the programs.

In particular, the first display control program P1, an extraction program P2, the second display control program P3, a creation program P4, an image DB 261, a medical information DB (medical information storage unit) 262, a set phrases DB (set phrase storage unit) 263, an interpretation report information DB 264, etc. are stored in the storage unit 26.

In the embodiment, the above mentioned programs P1 to P5 are stored in the storage unit 26. However, the programs may be SaaS (Software as a Service) type programs which are to be downloaded by accessing an outer data management server via internet when activating the medical information processing apparatus 20.

The first display control program P1 is a program to make the control unit 21 realize a function for displaying a medical image in the display unit 23, for example. The control unit 21 functions as the first display control unit by executing the first display control program P1.

The extraction program P2 is, for example, a program to make the control unit 21 realize a function for converting position information of a focus position to position information in a model image (described later) when the operating unit (specifying unit) 22 specifies the focus position in the medical image displayed in the display unit 23 and extracting the medical information corresponding to the position information in the model image from the medical information DB 262. The control unit 21 functions as an extraction unit by executing the extraction program P2.

The second display control program P3 is, for example, a program to make the control unit 21 realize a function to display the medical information extracted by the execution of the extraction program P2 as a selection candidate in the display unit 23. The control unit 21 functions as the second display control unit by executing the second display control program P3.

The creation program P4 is, for example, a program to make the control unit 21 realize a function to create an interpretation report by using the selected piece of medical information when the piece of medical information is selected by the operating unit (selection unit) 22 from the selection candidates displayed in the display unit 23. The control unit 21 functions as a creation unit by executing the creation program P4.

The image DB 261 is a database to store image data of a medical image which is sent from the modality 10 or the medical image server 30 and received by the communication unit 24 so as to be associated with patient information.

The medical information DB 262 is referred to when the extraction program P2 is executed, for example.

The medical information DB 262 is a database to store at least one item indicating an anatomical section of a human body (medical information) and position information of a predetermined region in a model image of a human body which are set in advance so as to be associated with each other.

FIG. 3 shows an example where the items (medical information) indicating anatomical sections of chest and position information of predetermined regions in a model image of a human body which is set in advance are associated with each other.

As shown in FIG. 3, as items indicating anatomical sections of chest, lung field (overall lung, apical pulmonary region, upper lung field, middle lung field, lower lung field, pulmonary hilar), mediastinum (pulmonary hilar, pulmonary artery, the first arch, the second arch, the third arch, the fourth arch, arch of azygos vein, main bronchus, trachea, upper mediastinum, anterior mediastinum, cardiophrenic angle, middle mediastinum, posterior mediastinum) are suggested.

For each of these items, position information of a predetermined region in a model image of a human body, which is set in advance, is associated.

In FIG. 3, "anatomical section: lower lung field" and the region A in the model image corresponding to the lower lung field, "anatomical section: pulmonary hilar" and the region B in the model image corresponding to the pulmonary hilar and "anatomical section: main bronchus" and the region C in the model image corresponding to the main bronchus are shown as examples.

As shown in FIG. 3, a reference region R (shown by dashed-dotted line in FIG. 3) which defines the reference anatomical region, which is used as the reference when the extraction program P2 is executed, is set in advance in the model image. Further, the coordinates (xm1, ym1) of the point R1 at the upper left corner of the reference region R and the coordinates (xm2, ym2) of the point R2 at the lower right corner of the reference region R are set.

Here, setting of the reference region R can be changed as a user desires. However, in the example shown in FIG. 3, the model image is the front chest image of a human body, and the anatomical region set in this model image is the thorax region including the lung field and the mediastinum which are most importance when making diagnosis with respect to a front chest image.

The fixed phrase DB 263 is referred to when the creation program P4 is executed, for example.

The fixed phrase DB 263 is, for example, a database for storing fixed phrases which are set in advance.

Fixed phrases are text information such as "abnormal shadow in ○○", for example, and such fixed phrase is input to the interpretation report creation screen g2 with the word expressing an anatomical section applied to "○○".

Here, the fixed phrases are not limited to the above and the setting can be changed arbitrarily. Further, different fixed phrases may be selected based on the items (medical information) indicating the anatomical sections.

The interpretation report information DB 264 is a database to store interpretation repot information created for each medical image.

Here, interpretation report information includes information such as finding information, medical procedure information, patient information (patient ID, patient name, gender, age, date or birth, etc.), date and the like.

Finding information is information that indicates findings on a medical image which is the diagnosis target, and is information including words and phrases indicating types of lesions, anatomical sections (medical information), level, condition, conclusion and the like.

Medical procedure information is information that indicates the diagnosis procedure performed on a patient, and for example, is information including words and phrases indicating name of illness, medication (prescription), treatment, injection, tests, operation, image reading, rehabilitation and the like.

[Operation of Medical Information Processing Apparatus]

Next, operation of the medical information processing apparatus 20 will be described.

FIG. 4 shows a flowchart of the selection candidate extraction process (steps S3 to S7) and the text creation process (step S8) which are executed by the medical information processing apparatus 20. These processes are realized by software processing by the cooperation between the control unit 21 and the programs P1 to P5 stored in the storage unit 26.

As the premise of these processes, it is assumed that the medical image obtained by picking up an image of a diagnosis target part of a diagnosis target patient with the modality 10 is stored in the medical image DB of the medical image server 30. Further, in the following description, the case where a front chest image is picked up as the diagnosis target part will be described as an example.

First, according to an operation by a physician who is a user through the operating unit 22, the control unit 21 obtains image data of a medical image, which is the diagnosis target, from the medical image server 30 via the communication unit 24 (step S1). Here, a medical image which is the diagnosis target is the newest medical image obtained by picking up an image of the diagnosis target patient, for example.

In particular, the control unit 21 sends the obtaining request of image data of a medical image which is the diagnosis target to the medical image server 30 via the communication unit 24. When the medical image server 30 receives the obtaining request of the medical image data sent from the medical information processing apparatus 20, the image data of the requested medical image is read out from the medical image DB and sent to the medical image processing apparatus 20. Then, the control unit 21 obtains the medical image data sent from the medical image server 30 and stores the obtained medical image data in the RAM 25.

Here, in the embodiment, image data of a medical image is obtained from the medical image server 30 as described above. However, image data of a medical image may be obtained from the modality 10.

Next, based on the obtained image data, the control unit 21 displays the medical image which is the diagnosis target on the report viewer screen G of the display unit 23 (step S2).

FIG. 5 shows an example of the repot viewer screen G which is displayed in the display unit 23.

The report viewer screen G includes a region 61 for displaying a viewer screen g1 and a region 62 for displaying an interpretation report creation screen g2.

The viewer screen g1 is provided with an image display region 611, an image processing tool display region 612 and the like.

The image display region 611 is a region for displaying a medical image which is the diagnosis target and past images of the patient who is currently the display target (the patient who is displayed in the patient information display region 63) for the purpose of diagnosis by a physician. In FIG. 5, a front chest image is displayed as the medical image which is the diagnosis target in the image display region 611.

The image processing tool display region 612 is a region for displaying a group of tool buttons used to give instructions for performing various image processing on the medical image displayed in the image display region 611.

The interpretation report creation screen g2 is a screen for creating an interpretation report regarding the medical image and is provided with a report display region 621, a past report selection region 622, a new report button 623 and the like.

The report display region 621 is a region for displaying a new report input region 621*a* for inputting a text of a new interpretation report and past interpretation reports 621*b* and 621*c* which are selected from the past report selection region 622. Here, by default, the two most recent past interpretation reports are displayed in the report display region 621.

The past report selection region 622 is a region for displaying a list of interpretation reports which are created in the past relating to the patient who is currently the display target (the patient displayed in the patient information display region 63).

The new report button 623 is a button for giving an instruction to display the new report input region 621*a* (open a new report) in the report display region 621.

The upper edge of the report viewer screen G is provided with a patient information display region 63 and display mode selection buttons 64*a* to 64*c*.

The patient information display region 63 is a region for displaying patient information of the patient who is currently the display target (diagnosis target).

The display mode selection buttons 64*a* to 64*c* are buttons for selecting a display mode of a screen in the display unit 23.

The display mode selection button 64*a* is a button for selecting the display mode of displaying the interpretation report creation screen g2 in the entire screen of the display unit 23.

The display mode selection button 64*b* is a button for selecting the display mode of displaying the report viewer screen G in the display unit 23. In FIG. 5, the display mode selection button 64*b* is selected.

The display mode selection button 64*c* is a button for selecting the display mode of displaying the viewer screen g1 in the entire screen of the display unit 23.

Next, the control unit 21 sets a diagnosis region r which is an anatomical region targeted for diagnosis in the medical image displayed in the display unit 23 (step S3).

The diagnosis region r is set at a position and over a range that covers the region required for making diagnosis on the target medical image. In the embodiment, with respect to the front chest image of FIG. 5, the thorax region including the lung field and the mediastinum, which are most important for making diagnosis, is set as the diagnosis region r.

Here, as a method for setting a diagnosis region r, the method described in JP 2864162 can be used, for example. This method will be described with reference to FIG. 6.

First, a projection prj (C) in the perpendicular direction of the region excluding the upper and lower parts of the image is obtained. In the projection prj (C), the line that passes the point where the signal value is the lowest in the center ⅓ portion obtained by dividing the projection prj (C) in three in the horizontal direction is the center line (XC). In the left and right ⅓ columns of the entire irradiation field, the points where the prj (C) first be at the thresholds TR and TL or smaller outside from the positions where the prj (C) are at the maximum are the left and right ends XR and XL of the thorax region.

Next, a projection prj (L) of the region between the left and right ends XR and XL in the horizontal direction is obtained. The point where the prj (L) first be at the threshold TT or smaller in the region of the irradiation field in the upper side from the line indicating the upper ¼ of the irradiation field is the upper end YT of the thorax region. The point where the prj (L) first be at the threshold TB or smaller in the region of the irradiation field in the lower side from the line indicating the ½ of the irradiation field is the lower end YB of the thorax region.

In such way, the thorax region whose upper, lower, left and right ends are extracted from the irradiation field is set as the diagnosis region r. Further, the coordinates (xi1, yi1) of the point r1 at the upper left corner of the diagnosis region r and the coordinates (xi2, yi2) of the point r2 at the lower right corner of the diagnosis region r are set.

Here, the method for setting the diagnosis region r is not limited to the above described method. That is, in the embodiment, the control unit 21 extracts the thorax region and sets the extracted thorax region as the diagnosis region r as described above. However, other than such configuration, a configuration where a physician who is a user performs setting manually by specifying an arbitrary diagnosis region r (thorax region) in the medical image displayed in the display unit 23 may be applied.

Further, the diagnosis region r is not limited to the thorax region and can be set arbitrarily by a user.

Next, by a physician who is a user operating the operating unit 22, a focus position in the medical image displayed in the display unit 23 is specified (step S4).

A focus position is a position for specifying a region where an abnormal shadow or the like exists, for example.

FIG. 7 shows an example of a state where a point in the medical image is specified through the operating unit 22 as the focus position. In FIG. 7, the arrow K is displayed at the specified position.

Next, the control unit 21 calculates the position of the focus position which is specified in the medical image on the model image (step S5).

The process of step S5 will be described with reference to FIGS. 8A and 8B.

FIG. 8A shows the medical image displayed in the display unit 23 and the diagnosis region r which is set in the medical image in step S3. FIG. 8B shows the model image which is stored in the medical information DB 262 in advance and the reference region R which is set in advance with respect to the model image.

In FIG. 8A, the coordinates of the point P which is specified in the medical image as the focus position are shown as (xi, yi).

Figure 8B:
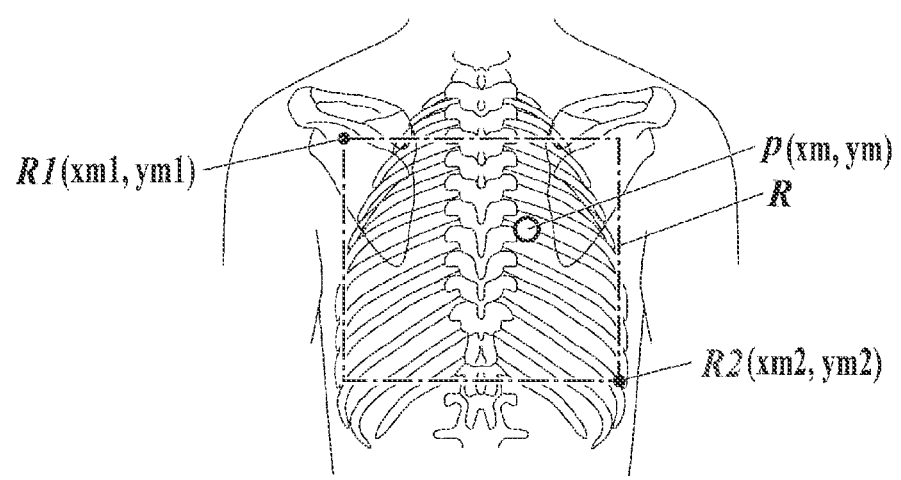
FIG. 8B is a view for explaining a process to calculate the position of the focus position in the medical image in the model image.

Further, in FIG. 8B, the coordinates of the point p in the model image corresponding to the focus position in the medical image are shown as (xm, ym).

The control unit 21 makes the diagnosis region r in the medical image and the reference region R in the model image associate to each other in accordance with the following formula (1). Therefore, in accordance with the formula (2), the position information (xi, yi) of the focus position in the medical image can be converted into the position information (xm, ym) in the model image.

$$(xi-xi1)/(xi2-xi1)=(xm-xm1)/(xm2-xm1)$$

$$(yi-yi1)/(yi2-yi1)=(ym-ym1)/(ym2-ym1) \quad \text{formula (1)}$$

$$xm=(xi-xi1)/(xi2-xi1) \times (xm2-xm1)+xm1$$

$$ym=(yi-yi1)/(yi2-yi1) \times (ym2-ym1)+ym1 \quad \text{formula (2)}$$

Next, based on the calculated position in the model image, the control unit 21 decides the pieces of medical information (the items indicating the anatomical sections of chest) to be displayed in the interpretation report creation screen g2 as selection candidates (step S6).

In particular, the control unit 21 compares the calculated position information in the model image (point p (xm, ym)) to the predetermined region in the model image of each piece of medical information (for example, regions A to C) to extract a selection candidate.

Figure 9A:
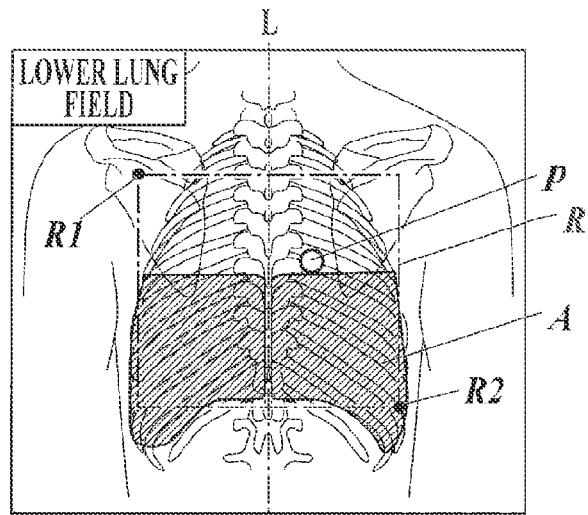
FIG. 9A is a view for explaining a process to decide a selection candidate.
Figure 9B:
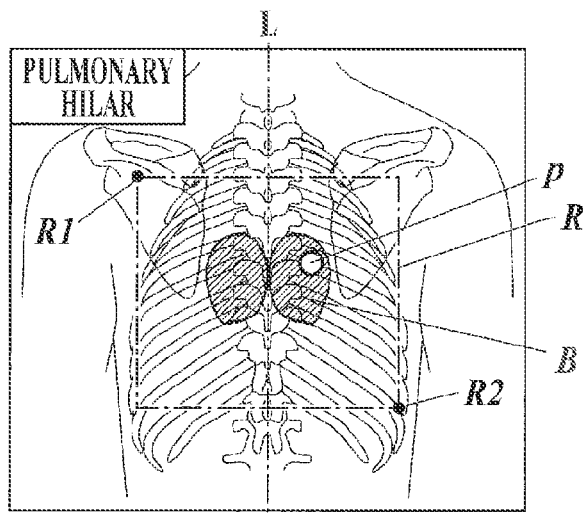
FIG. 9B is a view for explaining the process to decide a selection candidate.
Figure 9C:
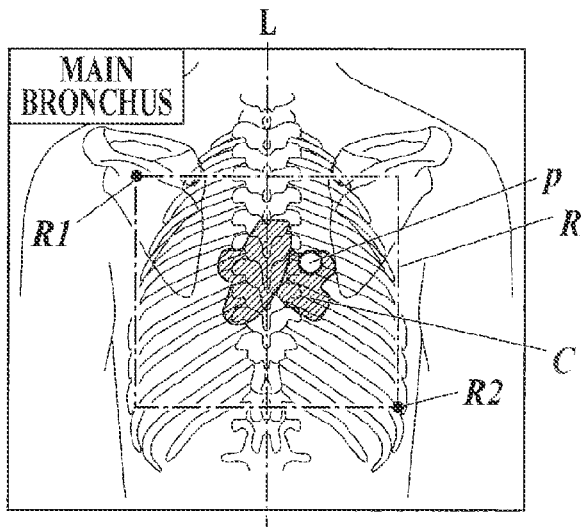
FIG. 9C is a view for explaining the process to decide a selection candidate.

FIG. 9A shows the positional relation between the lower lung field region A and the point p, FIG. 9B shows the positional relation between the pulmonary hilar region B and the point p and FIG. 9C shows the positional relation between the main bronchus region C and the point p, for example.

In the examples shown in FIGS. 9A to 9C, it can be seen that the lower lung field region A and the point p do not overlap and that the pulmonary hilar region B and the point p and the main bronchus region C and the point p overlap.

In such way, the control unit 21 compares the position of the point p and the region in the model image for each item indicating an anatomical section and determines whether the point p and the region overlap.

In a case where the point p and the region do not overlap, the control unit 21 pulls up the flag "1: display" and in a case where the point p and the region do not overlap, the control unit 21 pulls up the flag "0: not display". The item of the anatomical section with the flag "1: display" is decided to be a selection candidate.

In the examples shown in FIGS. 9A to 9C, since the flag "1" is pulled up with respect to each of the pulmonary hilar and the main bronchus, the pulmonary hilar and the main bronchus are decided to be selection candidates.

Further, with respect to each of the items of the anatomical sections with the flag "1: display" (the items which are decided to be selection candidates), the control unit 21 determines whether the position of the point p is on the left side or the right side of the center line L of the model image and attaches the word "left" or "right" to each of the selection candidates.

In the examples shown in FIGS. 9B and 9C, since the points p are on the left side of the center line L, it is decided to attached the word "left".

In the embodiment, the flag "1: display" or the flag "0: not display" is pulled up and then, the word "left" and "right" is attached to the item which is decided to be a selection candidate as described above. However, each of the items of the anatomical sections may have the word "left" or "right" attached thereto in advance.

Next, the control unit 21 makes the selection candidates be displayed in the report viewer screen G in the display unit 23 (step S7).

For example, the control unit 21 displays the selection dialog G1 in which selection candidates are shown so as to be selectable on the report viewer screen G.

Figure 10:
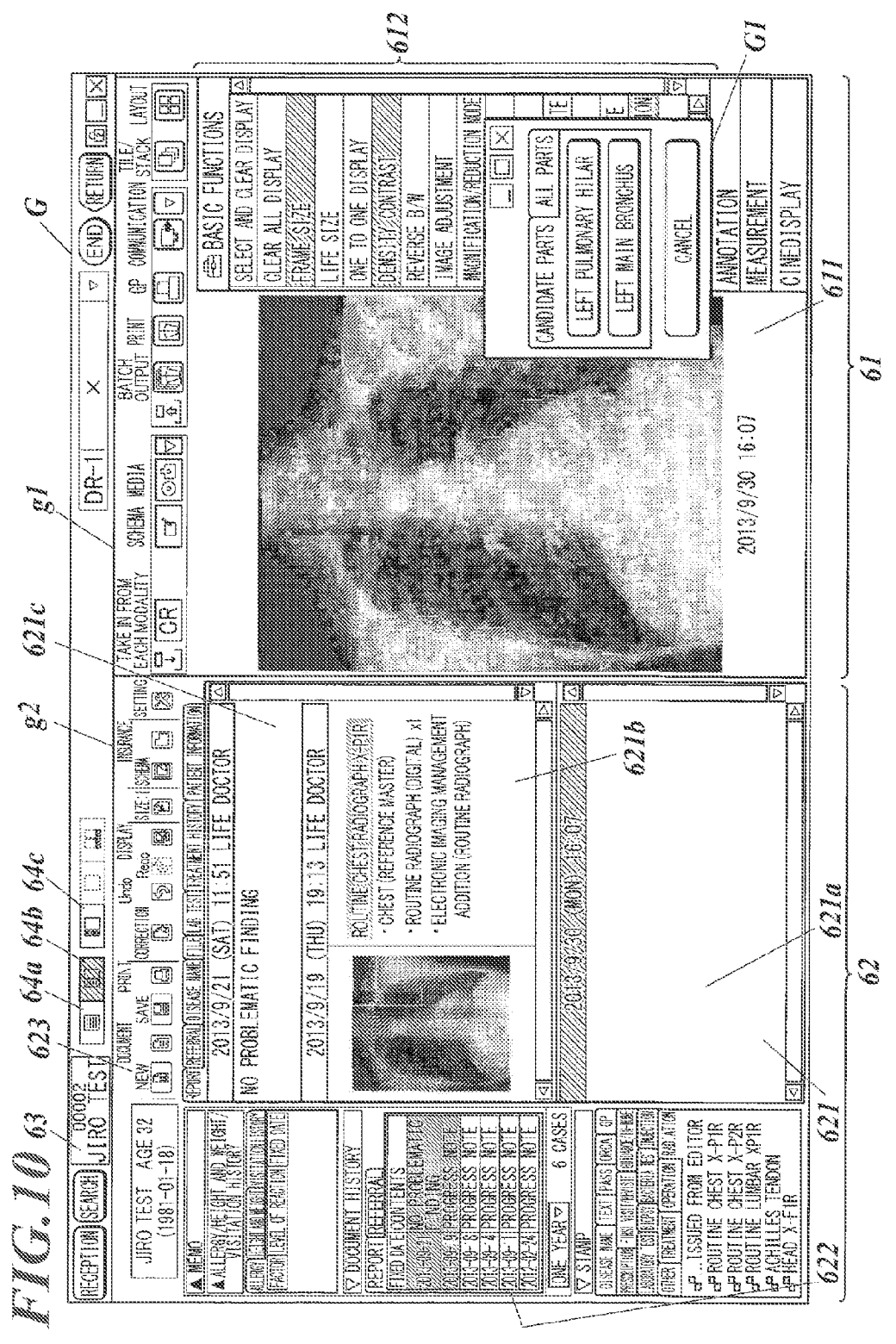

FIG. 10 shows an example where the selection dialog G1 is displayed on the report viewer screen G. In the selection dialog G1 shown in FIG. 10, the items "left pulmonary hilar" and "left main bronchus" are displayed so as to be selectable.

Next, when a physician who is a user operates the operating unit 22 and selects any of the selection candidates displayed in the selection dialog G1, the control unit 21 creates a text by integrating the content of the selected item in a fixed phrase and displays the created text in the interpretation report creation screen g2 as the interpretation report (step S8).

Figure 11:
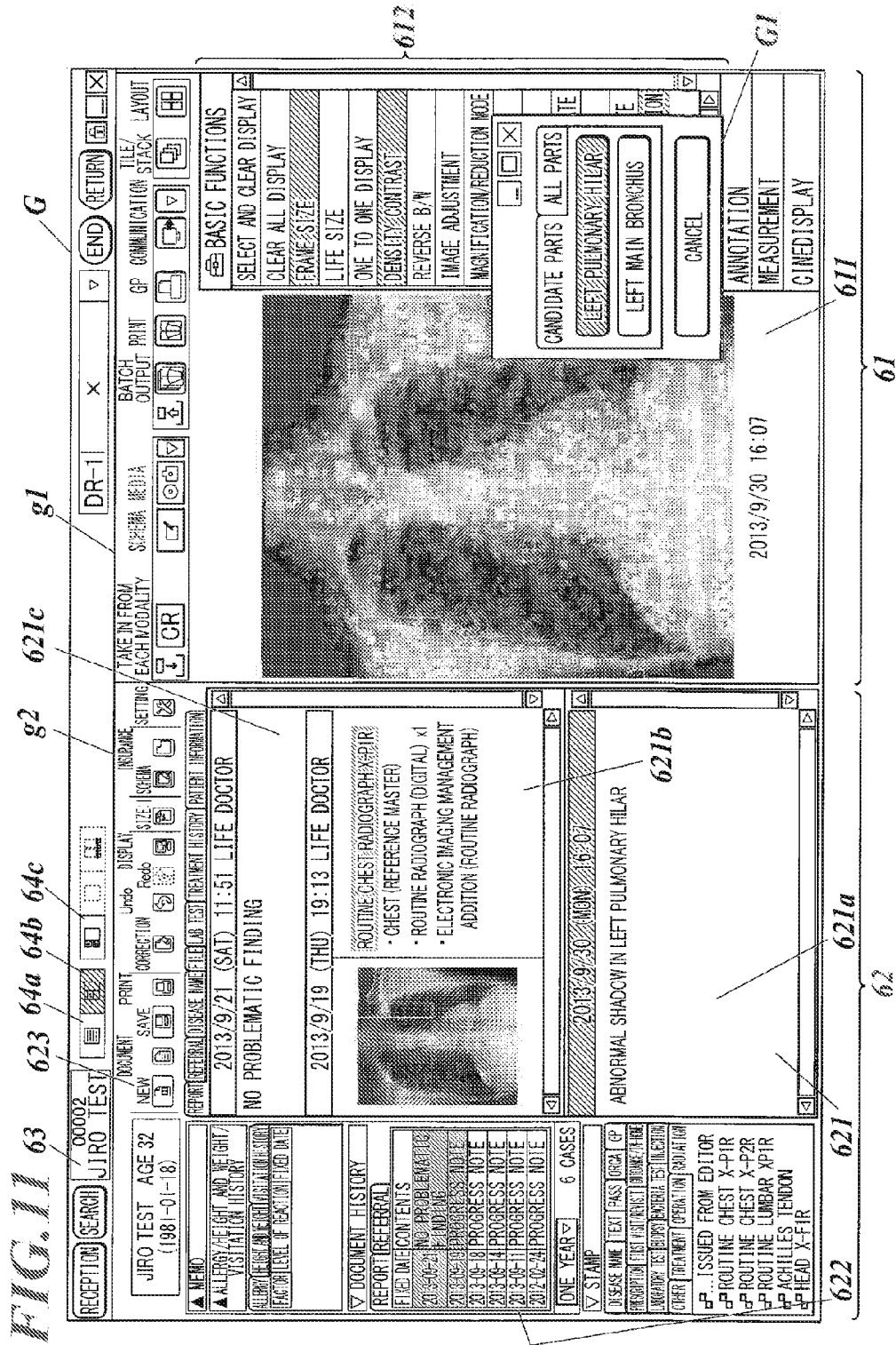
FIG. 11 is a view showing an example of a state where an interpretation report is input in a repot creation screen of a repot viewer screen.

FIG. 11 shows an example of a state where an interpretation report is displayed in the interpretation report creation screen g2.

In FIG. 11, the item "left pulmonary hilar" in the selection dialog G1 is selected and the interpretation report of "abnormal shadow in left pulmonary hilar" is displayed in the interpretation report creation screen g2.

In such way, according to the processing of steps S1 to S8, when a physician who is a user specifies a focus position in the displayed medical image, only the related medical information is extracted and displayed as selection candidates according to the specified position. Then, when the user selects any of the displayed selection candidates, an interpretation report including the content of the selected item is to be displayed.

In the processing of steps S1 to S8, since the processing of setting a diagnosis region r (extraction of the thorax region) in step S3 is the only image analysis processing, the overall processing speed can be fast and the processing results can be obtained quickly. That is to say, the waiting time until the selection dialog G1 is displayed after a medical image is displayed in the display unit 23 can be short. Further, setting of a diagnosis region r in step S3 may be performed by a user manually. In such case, the overall processing speed can be faster even more.

To add an item indicating an anatomical section (medical information), it is sufficient that an arbitrary item and the corresponding region thereof are set additionally in the medical information DB 262. To correct the reference for narrowing down the selection candidates, the reference region R in the model image or the region of each item should be corrected and there is no need to perform a new image recognition processing. Therefore, adding of medical information which is a selection candidate and correcting of the reference for narrowing down the selection candidates can be performed easily.

As described above, according to the embodiment, the apparatus is provided with the medical information DB 262 in which position information in a model image of a human body which is defined in advance and medical information (items indicating anatomical sections) are stored so as to be associated with each other. Further, according to the embodiment, when a focus position is specified in the medical image displayed in the display unit 23, the control unit 21 converts the position information of the specified focus position into position information on a model image, extracts the medical information corresponding to the position information on the model image from the medical information DB 262 and displays the extracted medical information in the display unit 23 as a selection candidate. Then, when a piece of medical information is selected from the selection candidates displayed in the display unit 23, the control unit 21 creates an interpretation report using the selected piece of medical information.

Therefore, the processing results can be obtained quickly because there is no need to execute number of complicated image analysis processing, and image reading and interpretation report creation can be started right after picking up a medical image.

Further, since the selection candidates relating to the specified focus position is extracted and displayed, a user can create a report just by selecting from the selection candidates relating to the specified focus position, and the workload relating to an interpretation report creation can be reduced.

Further, adding of medical information which is a selection candidate and correction of the reference for narrowing down the selection candidates can be performed easily and the operability of the apparatus is good.

Thus, the efficiency of creating a report at the time of image reading can be improved.

Moreover, according to the embodiment, the apparatus is provided with the fixed phrase DB 263 in which fixed phrases which are set in advance are stored. Further, according to the embodiment, when a piece of medical information is selected from the selection candidates displayed in the display unit 23, the control unit 21 creates a text by combining the selected piece of medical information and a fixed phrase stored in the fixed phrase DB 263.

Therefore, an interpretation report can be created just by selecting a desired item and the trouble of inputting a text can be avoided.

Furthermore, according to the embodiment, the reference region R defining the anatomical region which is the reference is set in advance in the model image. Further, according to the embodiment, the control unit 21 makes the anatomical region (diagnosis region r) recognized in the medical image and the reference region R set in the model image be associated to each other and converts the position information of the focus position in the medical image into the position information in the model image.

Therefore, the diagnosis region r in the medical image is in compliance with the reference region R which is set in advance in the model image and selection candidates can be extracted more accurately.

Moreover, according to the embodiment, a medical image is the thorax image of a human body and the anatomical region recognized in the medical image is a region including the thorax (thorax region).

Therefore, in the case where the medical image is the thorax image of a human body, the thorax region including the lung field and the mediastinum which are most important when making diagnosis on this region will be recognized as the anatomical region.

Further, according to the embodiment, the control unit 21 makes the image display screen for displaying a medical image and the report creation screen for displaying an interpretation report be displayed in the display unit 23 simultaneously.

Therefore, an interpretation report can be created while making diagnosis on a medical image.

Here, in the embodiment, description is given by using items indicating the anatomical sections as an example of medical information. However, medical information is not limited to this. For example, items indicating types of lesions (lesion names) as medical information and predetermined regions in a model image may be associated with each other and the types of lesions may be displayed as selection candidates.

Further, the order of priority of the pieces of medical information which are extracted as selection candidates may be decided based on predetermined priority level values and the selection candidates may be displayed in the display unit 23 according to the order of priority.

Figure 12:
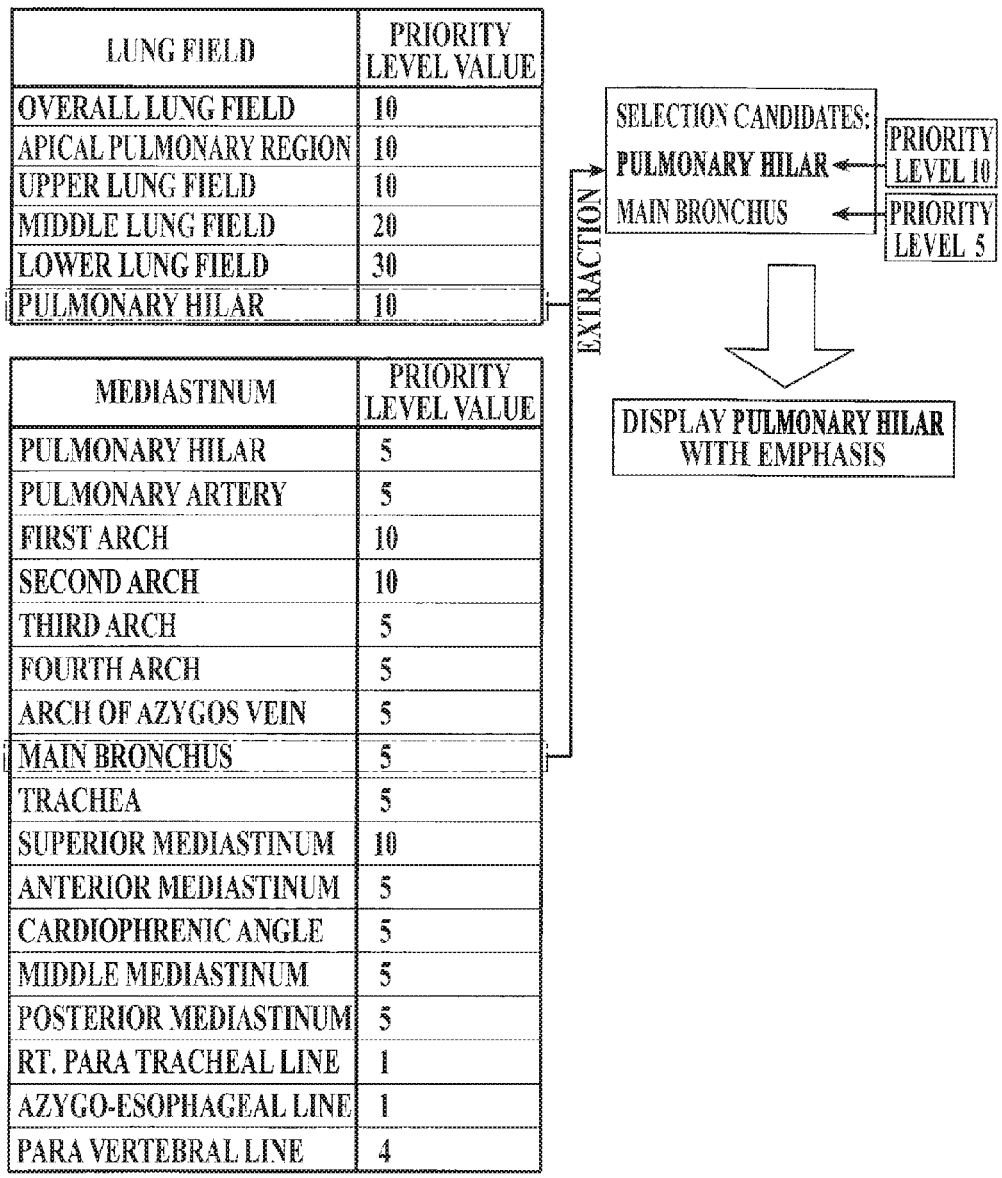
FIG. 12 is a diagram for explaining the order of priority.

In particular, as shown in FIG. 12, a priority level value may be set for each piece of medical information, the order of priority may be decided so that the greater the priority level value, the higher the priority, and the way of displaying the selection candidates may be changed according to the order of priority.

Here, as for the method for changing the way of displaying, display methods emphasizing the selection candidate having higher priority are suggested. Display with emphasis includes, for example, changing color, changing thickness of letters and the like. According to such display method, the selection candidate having higher priority is emphasized and is easy to find. This is especially effective in a case where the number of selection candidates is large.

Further, as for the way of changing the display method, the display method where the selection candidates having higher priority are arranged at the top of the selection dialog G1 is suggested, for example, other than the above mentioned methods. According to such display method, since the selection candidates having higher priority and expected to be selected are arranged at the top, the number of times of scrolling can be reduced in the case where the number of selection candidates is large.

Further, a display method where the selection candidate having the highest priority be in the selected state at the time when the selection dialog G1 is displayed in the display unit 23 may be applied. According to such display method, since the selection candidate having the highest priority and having the highest possibility to be selected is in the selected state, the trouble of selecting a selection candidate can be spared.

Further, as the way to set priority level values, there is a method where priority level values are set to the selection candidates arbitrarily by a user in the order of expected using frequency. For example, since a lesion recognized in a front chest image is often in lungs, the priority level values of the items of lungs may be set so as to have higher priority level values.

Further, by setting so as to count the number of times an item is used every time the item is used, the priority level value thereof can be set on the basis of the frequency of usage in the past.

Further, a method where priority level values are set according to the specified focus positions may be applied.

According to such setting method, the reference position is set in the region of each item indicating an anatomical section in advance. As for the reference position, the center of the region of the item indicating an anatomical section may be set as the reference position, for example. However, a user may arbitrarily se the reference position.

Then, the distance from the position (position p which is the position of the focus position in the model image) of each selection candidate obtained in step S5 to the reference position is calculated, and the priority level value is set so that the shorter the distance, the higher the priority level value. Here, a plurality of reference positions may be set in a region. In such case, the minimum value of the distances from the position of each selection candidate obtained in step S5 to the reference positions is used to set the priority level value.

Moreover, the priority level values may be changed according to the signal value or the edge information at the position P of the specified focus position. For example, in a case of low signal value (black part in the image), the possibility that the focus position is the lung field is high, and therefore, the priority level values of the items in lung can be set high. Further, in a case where the focus position is near the center of the left and right thorax and edge is strong, the priority level values of the items in mediastinum can be set high.

Furthermore, in the above embodiment, a configuration where one point in a medical image is specified to specified the focus position is described as an example. However, two points or more may be specified in a medical image to specify the focus position. This is effective especially in a case where the focus position covers relatively large range.

In a case where the focus position is specified with two points or more, the control unit 21 performs processing according to the region covering the two points.

For example, in a case where the upper and lower parts in a medical image are specified, the control unit 21 sets the priority level value of "overall lung field" be high.

Further, in a case where the left and right parts of a medical image are specified, the control unit 21 sets "both sides" as the word to be added when displaying the selection candidates.

Although the present invention has been described and illustrated in detail, it is clearly understood that the same is byway of illustrated and example only and is not to be taken byway of limitation, the scope of the present invention being interpreted by terms of the appended claims.

The entire disclosure of Japanese Patent Application No. 2013-241829 filed on Nov. 22, 2013 including description, claims, drawings, and abstract are incorporated herein by reference in its entirety.

What is claimed is:

1. A medical information processing apparatus, comprising:
   a medical information storage unit in which a piece of position information in a model image of a human body, the piece of position information being set in advance, and a piece of medical information are stored so as to be associated with each other;
   a first display control unit which displays a medical image in a display unit;
   a specifying unit which specifies a focus position in the medical image displayed in the display unit;
   an extraction unit which converts a piece of position information of the focus position specified by the specifying unit into a piece of position information in the model image and which extracts a piece of medical information corresponding to the piece of position information in the model image from the medical information storage unit;
   a second display control unit which displays the piece of medical information extracted by the extraction unit in the display unit as a selection candidate;
   a selection unit which selects a piece of medical information from the selection candidates displayed in the display unit; and
   a creation unit which creates an interpretation report by using the piece of medical information selected by the selection unit.

2. The medical information processing apparatus of claim 1, further comprising a set phrase storage unit in which a set phrase is stored, the set phrase being set in advance, wherein
   when the selection unit selects the piece of medical information from the selection candidates displayed in the display unit, the creation unit creates a text by combining the selected piece of medical information and the set phrase stored in the set phrase storage unit.

3. The medical information processing apparatus of claim 1, wherein
   a reference region which defines an anatomical region which is used as a reference is set in the model image in advance, and
   the extraction unit makes an anatomical region recognized in the medical image and the reference region set in the model image be associated to each other and converts the piece of position information of the focus position in the medical image into a piece of position information in the model image.

4. The medical information processing apparatus of claim 3, wherein
   the medical image is a chest image of a human body, and
   the anatomical region recognized in the medical image is a region including a thorax.

5. The medical information processing apparatus of claim 1, wherein the extraction unit decides order of priority of the pieces of medical information extracted as the selection candidates on a basis of predetermined priority level values, and the second display control unit displays the selection candidates in the display unit according to the order of priority.

6. The medical information processing apparatus of claim 5, wherein the predetermined priority level values are priority level values set in advance by a user, priority level values based on frequency of usage in past or priority level values obtained according to the specified focus position.

7. The medical information processing apparatus of claim 1, wherein the first display control unit displays an image display screen for displaying the medical image and a report creation screen for displaying the interpretation report simultaneously in the display unit.

8. The medical information processing apparatus of claim 1, wherein a plurality of reference regions, each defining an anatomical region, are set in advance in the model image, and position information is associated with each of the plurality of reference regions in the model image.

* * * * *